United States Patent [19]
Chartrain et al.

[11] Patent Number: 5,846,791
[45] Date of Patent: Dec. 8, 1998

[54] N-(R)-(2-HYDROXY-2-PYRIDINE-3-YL-ETHYL)-2-(4-NITRO-PHENYL)-ACETAMIDE

[75] Inventors: Michel M. Chartrain, Westfield; John Y. L. Chung, Edison; Christopher Roberge, Westfield, all of N.J.

[73] Assignee: Merck & Co., Inc., Rahway, N.J.

[21] Appl. No.: 883,255

[22] Filed: Jun. 26, 1997

Related U.S. Application Data

[60] Provisional application No. 60/022,055 Aug. 22, 1996.
[51] Int. Cl.⁶ .................................................. C12P 17/12
[52] U.S. Cl. .................. 435/122; 435/171; 435/255.4; 435/921
[58] Field of Search .................................. 435/122, 171, 435/255.4, 921

[56] References Cited

U.S. PATENT DOCUMENTS 5,561,142  10/1996  Fisher .................................... 514/312

FOREIGN PATENT DOCUMENTS

| 0 538 693 | 4/1993 | European Pat. Off. . |
|---|---|---|
| WO 88/03568 | 3/1988 | WIPO . |
| WO96/02657A1 | 7/1995 | WIPO . |

*Primary Examiner*—Herbert J. Lilling
*Attorney, Agent, or Firm*—Mollie M. Yang; David L. Rose

[57] ABSTRACT

Asymmetric bioreduction of a ketone substrate with yeast produces the corresponding (R)-alcohol of structure:

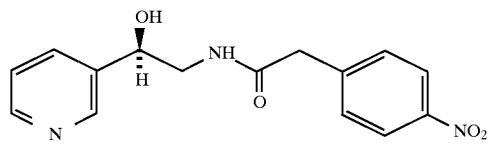

a key intermediate in the synthesis of a $\beta_3$-agonist of structure

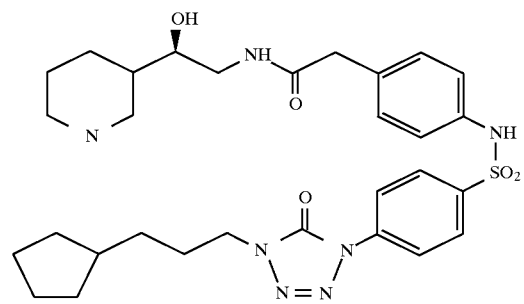

6 Claims, No Drawings

N-(R)-(2-HYDROXY-2-PYRIDINE-3-YL-ETHYL)-2-(4-NITRO-PHENYL)-ACETAMIDE

CROSS REFERENCE TO RELATED APPLICATIONS

This application is based on, and claims priority from provisional application 60/022,055 filed on Jul. 22, 1996.

SUMMARY OF THE INVENTION

This invention is concerned with a novel process for the synthesis of compound, I, a key intermediate in the synthesis of an important $\beta_3$-agonist, II, useful in the treatment of diabetes and obesity:

BACKGROUND OF THE INVENTION

The $\beta_3$-agonist, II, and the key intermediate, I, produced by the novel process of this invention, are known compounds, being described in Patent Publication WO 95/29159. Processes for the preparation of Compounds I and II are also disclosed in WO 95/29159. However, the process to the intermediate I involves a chiral borane reduction of a pyridyl chloromethyl ketone hydrochloride followed by formation of the epoxide from the resulting chloromethyl pyridyl methanol and then opening of the epoxide with the appropriate amine.

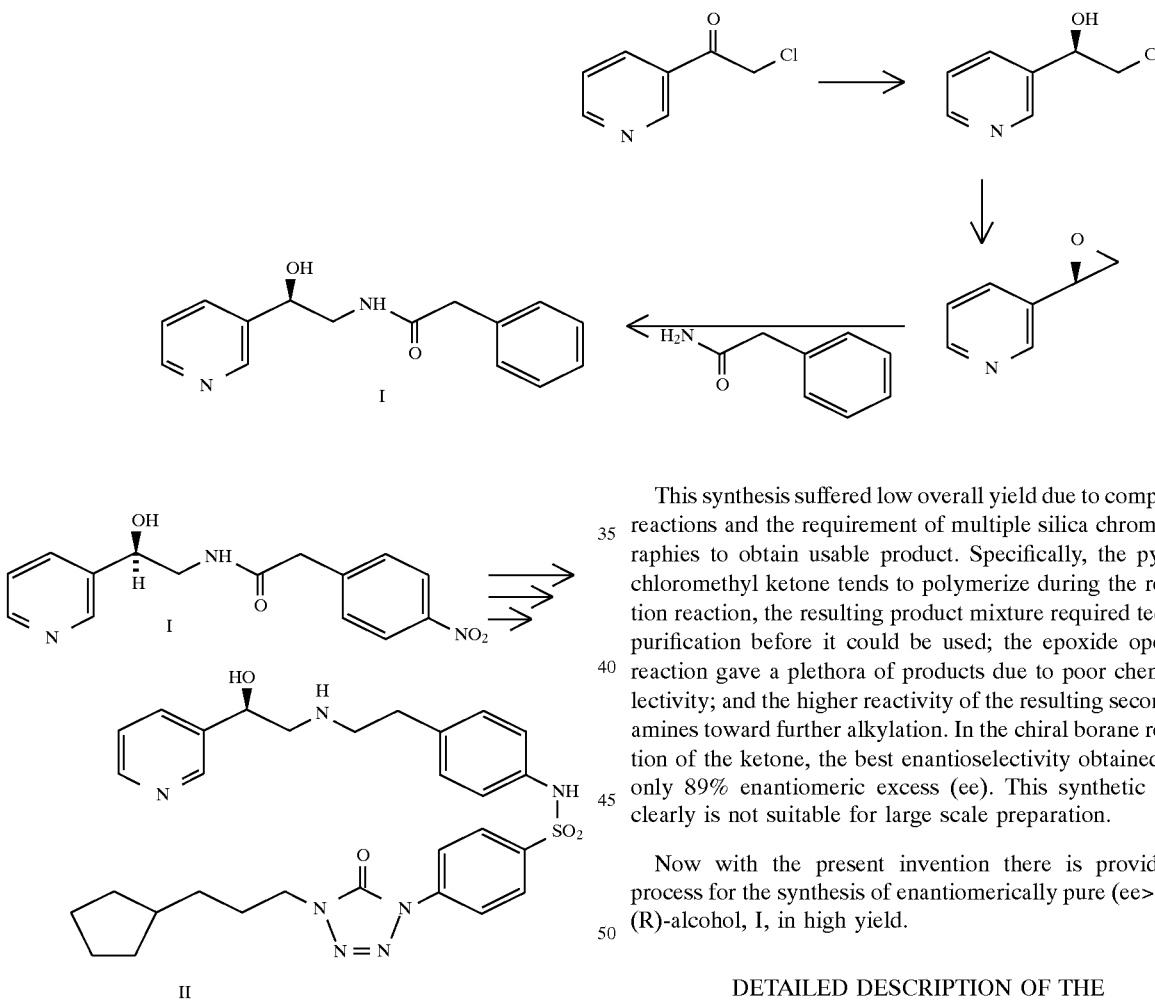

This synthesis suffered low overall yield due to competing reactions and the requirement of multiple silica chromatographies to obtain usable product. Specifically, the pyridyl chloromethyl ketone tends to polymerize during the reduction reaction, the resulting product mixture required tedious purification before it could be used; the epoxide opening reaction gave a plethora of products due to poor chemoselectivity; and the higher reactivity of the resulting secondary amines toward further alkylation. In the chiral borane reduction of the ketone, the best enantioselectivity obtained was only 89% enantiomeric excess (ee). This synthetic route clearly is not suitable for large scale preparation.

Now with the present invention there is provided a process for the synthesis of enantiomerically pure (ee>98%) (R)-alcohol, I, in high yield.

DETAILED DESCRIPTION OF THE INVENTION

The novel process of this invention comprises incubating a compound of structural formula III

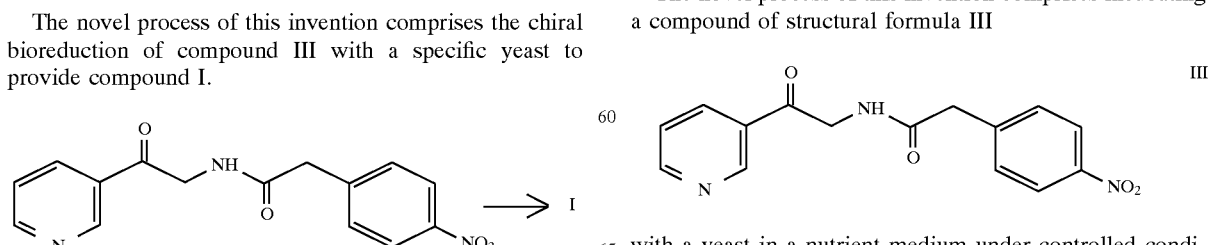

with a yeast in a nutrient medium under controlled conditions to produce enantiomerically pure (ee>98%) (R)-alcohol of structural formula I.

The novel process of this invention comprises the chiral bioreduction of compound III with a specific yeast to provide compound I.

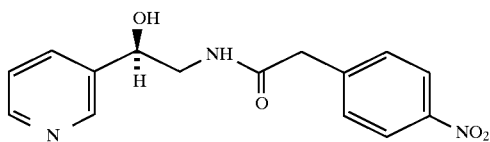

Many yeasts are capable of causing this asymmetric reduction with fairly high optical purity and good conversion of substrate to (R)-alcohol. However, one has been identified as most useful for this novel process providing >97% conversion of substrate to the (R)-alcohol of >97% enantiomeric excess (ee). That yeast is identified as a *Candida sorbophila*, number MY 1833 in the Merck & Co., Inc. collection of yeasts. It has been deposited with ATCC on Apr. 4, 1996 and received Accession No. 74362.

The nutrient medium employed in the novel process can be any medium known to be useful for growing yeast by those skilled in this art. The media are composed of buffers such as 4-morpholinepropanesulfonic acid (MOPS), 2-(N-morpholino)ethanesulfonic acid (MES), or citrate; yeast extracts; carbohydrates such as glucose, sucrose, fructose, or glycerol; various inorganic salts to provide minerals such as magnesium, calcium, copper, potassium and sodium; and an antifoam agent such as Dow P-2000.

The fermentation conditions that should be controlled for optimum results are starting pH between 4 and 9; airflow of about 0.25–5 L/m; a temperature of about 25°–35° C.; and dissolved oxygen above about 30% of saturation.

EXAMPLE 1
Growth of Seed Train

The contents of one 1-mL frozen vial of Y1833 (*Candida sorbophila*) in Saboraud Dextrose Broth were added to a 250-ml Erlenmeyer flask containing 50 ml of STAT1 medium described below that had been autoclaved for 30 minutes at 121° C. The culture was allowed to grow for 24 hours at 30° C. on an orbital shaker at 200 RPM. From this flask, 10 mL of inoculum were added to a 2-L Erlenmeyer flask containing 500 ml of STAT1 medium that had been autoclaved for 30 minutes at 121° C. This culture was also allowed to grow for 24 hours at 30° C. on an orbital shaker at 200 RPM. The contents of this flask were used as inoculum for a 16 L fermentation.

STAT1 medium consists of monosodium glutamate (20 g/L); MOPS (20 g/L); yeast extract (7 g/L); glucose (2 g/L); P-2000 (2 ml/L); Magnesium chloride hexahydrate (1 g/L); calcium chloride dihydrate (0.5 g/L); cupric chloride dihydrate (0.5 g/L); and potassium chloride (0.5 g/L).
Fermentations The fermentation medium (STAT1, 16L) was added to the fermentation tank and sterilized for 35 min. at 123° C. The pH of the broth was adjusted to 6.0–6.5 by the addition of HCl. In addition to a 6.5 pH, the other initial conditions of the fermenters were an agitation of 600 RPM, an airflow of 4L/min, a temperature of 30° C., and a pressure of 1 bar. The dissolved oxygen in the fermenter was maintained above 30% of saturation through automated agitation control in the range between 600 and 700 RPM.

A substrate addition assembly was constructed by connecting a fermenter needle to approximately four feet of silicone rubber tubing (0.192" I.D.×0.392" O.D.) attached to a 2-L bottle with a bottom spout, and to this 320 mL of pH 2 deionized water and a magnetic stir bar were added. The deionized water was acidified with phosphoric acid prior to adding it to the bottle. The assembly was autoclaved for 30 minutes at 121.5° C. After the equipment had cooled to room temperature, 40 g ketone substrate (Compound III) were measured in a weigh boat and added to the bottle using a metal spatula under a sterile hood. The weigh boat and spatula were then rinsed with 320 mL ethanol which was also added to the bottle under a fume hood. The assembly was placed on a stir plate that was used to agitate the mixture and create a suspension. The pressure in the tank was then reduced to 0.1 bar and the airflow was stopped while the suspension was pumped through the tubing and needle into the fermenter. Next, 320 mL deionized water that had been autoclaved for 30 minutes at 121° C. were poured into the bottle and stirring and pumping were resumed to wash any remaining substrate into the tank. Finally, 500 mL inoculum were poured into the bottle, and again stirring and pumping were resumed. After the culture had been transferred to the fermenter, the tubing was clamped and the pressure and airflow of the tank were returned to their initial values.

The concentrations of ketone and alcohol (Compound I) in broth samples were assayed by reverse phase HPLC (ODS-AQ column; [acetonitrile with 0.1% $H_3PO_4$]: [water with 1.77 g/l $NaH_2PO_4$ and 0.30 g/l $Na_2HPO_4$] mobile phase in a gradient from 10:90 to 80:20 over 20 min; 1.0 ml/min flow rate; 220 nm detection; and retention times of 12.6 min [alcohol] and 14.5 min [ketone]) and the e.e. of the alcohol was monitored by supercritical fluid HPLC (Chiralcel OD-H column; 300 bar column pressure; 35° C. column temperature; modifier of 19% (v/v) methanol containing 20 mmol trichloroacetic acid; 1.0 ml/min flow rate; 260 nm detection; and retention times of 8.6 min [(R)-alcohol], 9.6 min [(S)-alcohol], and 13.7 min [ketone]). The runs were terminated after approximately 45 hours, when the amount of ketone in the fermenter as assayed by HPLC had reached <1% of its initial value and approximately 2.5 g/l alcohol were in the tank.
Isolation The fermentation batch was centrifuged to remove cells and fines.

Supernatant (170 mL) was extracted twice with 170 mL methyl ethyl ketone (MEK) saturated with water. The combined MEK extracts were concentrated to an aqueous slurry, sulfuric acid was added to pH2 and the slurry was extracted three times with isopropyl acetate/5% (v/v) isopropyl alcohol. The pH of the washed aqueous slurry was adjusted to 6.8 with 50% aqueous sodium hydroxide, following which fine crystalline solids gradually appeared.

The aqueous slurry was concentrated under vacuum to remove organic solvents. The room temperature aqueous slurry was filtered to collect the solid product and the filter cake was washed with cold water. Yield ~70% (28 g); Purity ~87%; ee 98.5%.

EXAMPLE 2
Seed Train

The contents of one 1-mL frozen vial of Y1833 (*Candida sorbophila*) preserved in Saboraud Dextrose Broth (Difco) and glycerol (20%, v/v) at −70° C. were added to a 250-mL Erlenmeyer flask containing 50 mL of Sabouraud Dextrose Broth medium that had been autoclaved for 30 minutes at 121.5° C. The culture was allowed to grow for 24 hours at 34° C. on an orbital shaker at 200 RPM.
Biotransformation A volume of 1 liter of YNB medium [monosodium glutamate (93 g/L); citrate monohydrate (20 g/L); yeast nitrogen base w/o amino acids and ammonium sulfate (15 g/L); P-2000 (10 mL/L); cupric chloride dihydrate (15 mg/L)] was added to the bioreactor (2 liter) and sterilized for 30 min. at 123° C. Glucose that had been sterilized separately was added upon cooling to give a final concentration of 7 g/L. A volume of 20 ml of the inoculum prepared as described above was then added to the bioreactor. The microorganisms were cultivated under an agitation of 1200 RPM, a sparging of 0.5L/min of 90% oxygen", and a temperature of 34° C., until an optical density (OD) @ 600 nm in the range of 15–25 and a glucose concentration of <1 g/L were achieved. At that time, the pH of the cultivation broth was adjusted to 8.0 and maintained at that value through the addition of sterile 5N NaOH and 5N $H_2SO_4$, ethanol in the amount of 13 ml and ketone substrate in the amount of 50 g were then charged to the tank. Immediately after these additions, glucose feeding was initiated at a rate of 1 g/(1·hr) from a 280 g/l stock solution that had been autoclaved for 30 min at 121.5° C. The concentrations of ketone and alcohol in the broth were assayed by reverse phase HPLC and the e.e. of the alcohol was monitored by supercritical fluid HPLC. The runs were terminated after approximately 7 days, when the amount of ketone in the fermenter as assayed by HPLC had reached <1% of its initial value (See Example 1 for HPLC method). A final alcohol titer of 35 g/L with an ee of 98% was achieved under these conditions.

Isolation

Isolation of the product is conducted in the same manner as described in Example 1.

What is claimed is:

1. A process for the preparation of a compound of structural formula I:

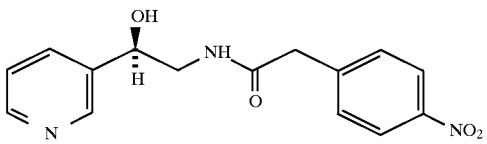

which comprises incubating a substrate of structural formula III:

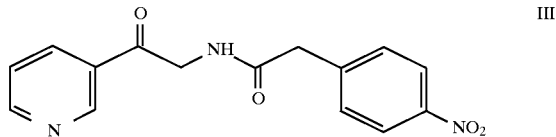

with *Candida Sorbophila*, ATCC Accension No. 74362 in a nutrient medium.

2. The process of claim 1 wherein the nutrient medium comprises monosodium glutamate; a buffer; yeast extract; a carbohydrate; inorganic salts and an antifoam agent.

3. The process of claim 2 wherein the initial pH is about 6.0–6.5; air flow of about 0.25–5 L/min; a temperature of about 25°–35° C.; and oxygen content above 30% of saturation.

4. The process of claim 3 wherein the nutrient medium comprises monosodium glutamate (20 g/L); MOPS (20 g/L); yeast extract (7 g/L); glucose (2 g/L); P-2000 (2 ml/L); magnesium chloride hexahydrate (1 g/L); calcium chloride dihydrate (0.5 g/L); cupric chloride dihydrate (0.5 g/L); and potassium chloride (0.5 g/L).

5. The process of claim 2 wherein the medium is agitated at about 1200 RPM, with an air-flow of about 0.5 L/min of 90% oxygen, at a temperature of about 34° C.

6. The process of claim 5 wherein the nutrient medium comprises monosodium glutamate (93 g/L); citrate monohydrate (20 g/L); yeast nitrogen base without amino acids, ammonium sulfate (15 g/L); P-2000 (10 mL/L); and cupric chloride dihydrate (15 g/L).

* * * * *

UNITED STATES PATENT AND TRADEMARK OFFICE
CERTIFICATE OF CORRECTION

PATENT NO. : 5,846,791

DATED : 12/8/98

INVENTOR(S) : MICHEL M. CHARTRAIN, JOHN Y. L. CHUNG, CHRISTOPHER ROBERGE

It is certified that error appears in the above-identified patent and that said Letters Patent is hereby corrected as shown below:

On the title page, Item [57],

In the Abstract

Delete "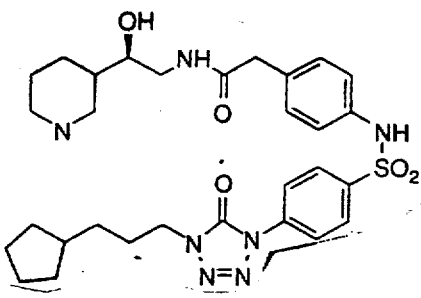"

and replace 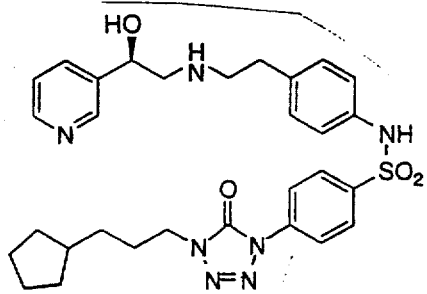

UNITED STATES PATENT AND TRADEMARK OFFICE
CERTIFICATE OF CORRECTION

PATENT NO. : 5,846,791
DATED : 12/8/98
INVENTOR(S) : Michel M. Chartrain, John Y.L. Chung, Christopher Roberge It is certified that error appears in the above-identified patent and that said Letters Patent is hereby corrected as shown below:

Column 3, line 32: delete "Y1833" and replace it with --MY1833--.

Column 4, line 52: delete "Y1833" and replace it with --MY1833--.

Signed and Sealed this

Twenty-ninth Day of June, 1999

Q. TODD DICKINSON

*Attest:*

*Attesting Officer*    Acting Commissioner of Patents and Trademarks